United States Patent [19]

Bolich, Jr. et al.

[11] Patent Number: 5,104,646

[45] Date of Patent: Apr. 14, 1992

[54] VEHICLE SYSTEMS FOR USE IN COSMETIC COMPOSITIONS

[75] Inventors: Raymond E. Bolich, Jr., Maineville; Michael J. Norton, Cincinnati; Glen D. Russell, Loveland, all of Ohio

[73] Assignee: The Procter & Gamble Company, Cincinnati, Ohio

[21] Appl. No.: 551,119

[22] Filed: Jul. 16, 1990

Related U.S. Application Data

[63] Continuation-in-part of Ser. No. 390,268, Aug. 7, 1989, abandoned.

[51] Int. Cl.$^5$ .................. A61K 7/08; A61K 7/48; A61K 7/13
[52] U.S. Cl. ..................... 424/70; 424/71; 8/405; 514/781
[58] Field of Search ............... 424/70, 71, 78, DIG. 1; 514/781; 8/405

[56] References Cited

U.S. PATENT DOCUMENTS

| | | | |
|---|---|---|---|
| 3,395,041 | 7/1968 | Hsiung | 132/7 |
| 3,579,632 | 5/1971 | Sonnen | 424/70 |
| 3,580,853 | 5/1971 | Parran | 252/152 |
| 3,723,325 | 3/1973 | Parran | 252/106 |
| 4,228,277 | 10/1980 | Landoll | 536/90 |
| 4,243,802 | 1/1981 | Landoll | 536/91 |
| 4,298,728 | 11/1981 | Majewicz et al. | 536/96 |
| 4,299,817 | 11/1981 | Hannon, III et al. | 424/70 |
| 4,331,167 | 5/1982 | Wajaroff | 132/7 |
| 4,336,246 | 6/1982 | Leon-Pekarek | 424/70 |
| 4,352,916 | 10/1982 | Landoll | 526/200 |
| 4,374,825 | 2/1983 | Bolich, Jr. et al. | 424/70 |
| 4,415,701 | 11/1983 | Bauer | 524/612 |
| 4,421,740 | 12/1983 | Burton | 424/70 |
| 4,426,485 | 1/1984 | Hoy et al. | 524/591 |
| 4,435,217 | 3/1984 | House | 106/171 |
| 4,458,068 | 7/1984 | Warner et al. | 536/91 |
| 4,459,285 | 7/1984 | Grollier et al. | 424/74 |
| 4,465,517 | 8/1984 | Shields | 106/35 |
| 4,485,089 | 11/1984 | Leipold | 424/49 |
| 4,496,708 | 1/1985 | Dehm et al. | 528/76 |
| 4,501,617 | 2/1985 | Desmarais | 106/93 |
| 4,523,010 | 6/1985 | Lukach et al. | 536/91 |
| 4,529,523 | 7/1985 | Landoll | 252/8.55 D |
| 4,557,928 | 12/1985 | Glover | 424/70 |
| 4,581,230 | 4/1986 | Grollier et al. | 424/74 |
| 4,584,189 | 4/1986 | Leipold | 424/54 |
| 4,610,874 | 9/1986 | Matravers | 424/70 |
| 4,683,004 | 7/1987 | Goddard | 106/170 |
| 4,684,704 | 8/1987 | Craig | 526/200 |
| 4,707,189 | 11/1987 | Nickol | 106/176 |
| 4,725,433 | 2/1988 | Matravers | 424/70 |
| 4,726,944 | 2/1988 | Oslpow et al. | 424/70 |
| 4,788,006 | 11/1988 | Bolich, Jr. et al. | 252/550 |
| 4,826,970 | 5/1989 | Reid et al. | 536/66 |
| 4,883,536 | 11/1989 | Burdick | 106/194 |
| 4,894,224 | 1/1990 | Kuwata et al. | 424/78 |
| 4,902,499 | 2/1990 | Bolich, Jr. et al. | 536/66 |

FOREIGN PATENT DOCUMENTS

| | | |
|---|---|---|
| 0170927 | 2/1986 | European Pat. Off. |
| 54-043210 | 4/1979 | Japan |
| 5900758 | 2/1984 | Japan |
| 60023151 | 6/1985 | Japan |
| 60026401 | 6/1985 | Japan |
| 61053211 | 3/1986 | Japan |
| 61-023764 | 6/1986 | Japan |
| 61-151105 | 7/1986 | Japan |
| 61-186306 | 8/1986 | Japan |
| 62195963 | 8/1987 | Japan |
| 62-294606 | 12/1987 | Japan |
| 2185269A | 7/1987 | United Kingdom |

OTHER PUBLICATIONS

Amer. Chem. Soc., Spring Mtg. 1987; Denver, Colo.; Symposium notes, Div. of polymeric Mat's: Science and Engineering, vol. 56, 56, presentation of A. Sau 194th Nat'l Mtg of ACS, New Orleans, La., Aug. 30–Sep. 4 1987; Glass, J. E., ed., Advances in Chem. Series, 0065-2393; 223, pp. 344–364.
Gelman, R. A., International Dissolving Pulp Conference, TAPPI, Feb. 1987, pp. 159–165.
Steiner, C. A., Polymer Prepr. (Am. Chem. Soc., Div. Polym. Chem.) 1985, 26(1), pp. 224–225.
Chem Abs. 103:27060b, Hercules Inc. Research Disclosure–252002, 1985 Publication.
Hercules Inc. Research Disclosure–252021.
Hercules Inc. Development Data–15 Publication.
Hercules Inc. Development Data–16 Publication.
Hercules Inc. Development Data–32 Publication.
Hercules Inc. Research Publication dated Nov. 2, 1984, entitled "Update WSP D–340 Performance in Surfactant Systems".
U.S. Serial No. 390,328, Bolich et al., filed Aug. 7, 1989.
U.S. Serial No. 390,330, Bolich et al., filed Aug. 7, 1989.

Primary Examiner—Thurman K. Page
Assistant Examiner—Susan S. Rucker
Attorney, Agent, or Firm—Leonard W. Lewis; Steven J. Goldstein

[57] ABSTRACT

Disclosed is a unique vehicle system which provides a desirable rheology to products formulated therewith, enhanced dispersion of actives therein, and improved deposition of actives therefrom. This vehicle system comprises a primary thickening agent which is a nonionic long chain alkylated water-soluble polymer, and a secondary thickening agent which is a water-soluble surfactant, dispersed in a compatible solvent. Optionally, a rheological aid, which is a chelating agent may be included in the vehicle system. Also, optionally, a distributing aid, which is a water-soluble polymer of either high molecular weight or strong ionic character may be included in the vehicle system. These vehicle systems are useful in cosmetic compositions which are used to deliver an active component to the hair or skin. The vehicle systems are particularly useful in hair care compositions, especially rinse-off hair conditioning compositions, because they effectively deliver the hair conditioning component to the hair without depositing a substantial amount of the vehicle material onto the hair.

49 Claims, No Drawings

VEHICLE SYSTEMS FOR USE IN COSMETIC COMPOSITIONS

TECHNICAL FIELD

This application is a continuation-in-part of U.S. application Ser. No. 390,268, Bolich et al., filed Aug. 7, 1989, now abandoned.

The present invention relates to novel vehicle systems, and cosmetic compositions formulated therewith, based on particular nonionic long chain alkylated water-soluble polymer derivatives and water-soluble surfactants at certain critical levels dispersed in a compatible solvent. A particularly useful application of the present invention is in hair care compositions, especially rinse-off hair conditioning compositions.

BACKGROUND OF THE INVENTION

Typical hair conditioning products have a particular thick rheology that is desirable for such products. These products are based on the combination of a surfactant, which is generally a quaternary ammonium compound, and a fatty alcohol. This combination results in a gel-network structure which provides the composition with a thick rheology. However, while such compositions deliver conditioning benefits to the hair, such compositions also deposit in hair making hair look and feel dirty.

Alternative thickening systems have been used in hair care compositions, but none have been found to date which provide this same desirable rheology. Though hair care products thickened with polymer thickeners can be made to have a thick rheology, these products generally are characterized by an undesirable "slimy"-feel and do not hold their poured shape.

Nonionic water-soluble cellulose ethers are employed in a variety of applications, including hair care compositions. Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Better thickening efficiency is realized with higher molecular weight cellulose ethers. However, production of such materials is difficult and expensive. Though crosslinking of these polymers is an alternative means to achieve high viscosity solutions, good crosslinking techniques are not known. Of course, high concentrations of polymers will also provide high viscosity but such an approach is inefficient and impractical, particularly due to the high expense involved. Furthermore, use of highly crosslinked polymers or high levels of polymeric thickeners may result in a vehicle system that is too elastic for the present uses.

Alternative water-soluble polymeric thickeners sometimes used to thicken hair care compositions are natural polysaccharides such as guar gum, xanthan gum and locust bean gum.

A number of references teach the use of nonionic cellulose ethers and water-soluble gums for thickening hair care compositions. See for example, U.S. Pat. No. 4,577,928, Glover, issued Dec. 10, 1985, teaching a hair conditioner comprising a suspension system which consists of one of glucan gum, guar gum, and hydroxyethylcellulose; and U.S. Pat. No. 4,581,230, Grollier et al;, issued Apr. 8, 1986, which teaches cosmetic compositions for treating hair which comprise as thickening agents hydroxyethylcellulose, or water-soluble vegetable thickening agents, such as guar gum. Japanese Patent Publication 61-053211, published Mar. 7, 1986, discloses a hair colorant containing an aromatic alcohol, xanthan gum, and hydroxyethylcellulose.

Certain cellulose ethers have been disclosed in U.S. Pat. No. 4,228,277, Landoll, issued Oct. 14, 1980, which are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to be modified is preferably one of low to medium molecular weight; i.e., less than about 800,000 and preferably between about 20,000 and 700,000 (about 75 to 2500 D.P.).

These modified cellulose ethers have been disclosed for use in a variety of composition types. Landoll ('277) teaches the use of these materials in shampoo formulations. Hercules trade literature teaches the use of these materials in shampoos, liquid soaps, and lotions. U.S. Pat. No. 4,683,004, Goddard, issued July 28, 1987, discloses the use of these materials in mousse compositions for the hair. U.S. Pat. No. 4,485,089, Leipold, issued Nov. 27, 1984, teaches dentifrice compositions containing these materials.

These materials have now been found to provide a rheology very much like the desirable gel-network structure of typical hair conditioners (without the slimy feel associated with most polymeric thickeners), when they are combined with surfactants at certain critical levels.

Hence, it is an object of the present invention to provide a vehicle system for hair care and other cosmetic compositions which provides a gel-network-like structure to the composition but which is not based on a typical quaternary ammonium compound/fatty alcohol gel-network thickening system.

It is also an object of the present invention to provide a vehicle system for hair care and other cosmetic compositions which allows for dispersion of a wide variety of active hair or skin care components therein.

It is also an object of the present invention to provide a vehicle system for hair care and other cosmetic compositions which will maximize deposition of the active hair or skin care component contained therein onto the hair or skin while minimizing deposition of the vehicle system components.

These other objects will become readily apparent from the detailed description which follows.

SUMMARY OF THE INVENTION

The present invention relates to unique vehicle systems for use in cosmetic compositions which are polymer-based but which provide a rheology to the cosmetic compositions which mimics gel-network systems. These vehicle systems are based on a two-component thickening system. More specifically, the cosmetic compositions of the present invention comprise:

(a) from about 80% to about 100% preferably from about 80% to about 99.9%, of a vehicle system which comprises:
   (A) from about 0.1% to about 10.0% by weight of the cosmetic composition of a hydrophobically modified nonionic water-soluble polymer which comprises a water-soluble polymer backbone and hydrophobic groups selected from the group consisting of $C_8$-$C_{22}$ alkyl, arylalkyl, alkylaryl groups and mixtures thereof; wherein the ratio of hydrophilic portion to hydrophobic portion of the polymer is from about 10:1 to about 1000:1; preferably the hydrophobically modified nonionic water-soluble polymer comprises a nonionic cellulose ether having a sufficient degree of nonionic substitution selected from the group consisting of methyl, hydroxyethyl, and hydroxypropyl to cause it to be water-soluble and being further substituted with a long chain alkyl radical having 10 to 22 carbon atoms in an amount between about 0.2 weight percent and the amount which renders said cellulose ether less than 1% by weight soluble in water;

(B) from about 0.02% to about 0.3% by weight of the cosmetic composition of a water-soluble surfactant having a molecular weight less than about 20,000;

(C) from about 65% to about 99% by weight of the cosmetic composition of a compatible solvent; and (b) from 0 to about 20%, preferably from about 0.1% to about 20%, of an active cosmetic component; wherein compositions comprising said vehicle system comprise no more than about 1.0%, preferably no more than 0.5%, total of water-soluble surfactant materials.

The vehicle system provides a rheology to the cosmetic compositions formulated therewith, that is preferably characterized by a shear stress of from 0 to about 50 pascal over a shear rate range of from about 0.04 $sec^{-1}$ to about 25 $sec^{-1}$. These vehicle systems are particularly useful in hair care compositions, especially rinse-off hair conditioners. Most preferably, the hair care compositions formulated with these unique vehicle systems comprise no more than about 1% of fatty alcohol materials.

DETAILED DESCRIPTION OF THE INVENTION

The essential as well as optional components of the present compositions are described below.

Primary Thickener

The vehicle systems of the present invention contain, as an essential component, a primary thickening material. The primary thickening material is a hydrophobically modified nonionic water-soluble polymer. By "hydrophobically modified nonionic water-soluble polymer" is meant a nonionic water-soluble polymer which has been modified by the substitution with a sufficient amount of hydrophobic groups to make the polymer less soluble in water. Hence, the polymer backbone of the primary thickener can be essentially any water-soluble polymer. The hydrophobic groups can be $C_8$ to $C_{22}$ alkyl, aryl alkyl, alkyl aryl groups and mixtures thereof. The degree of hydrophobic substitution on the polymer backbone should be from about 0.10% to about 1.0%, depending on the particular polymer backbone. More generally, the ratio of hydrophilic portion to hydrophobic portion of the polymer is from about 10:1 to about 1000:1.

A number of existing patents disclose nonionic polymer materials which meet the above requirements and which are useful in the present invention. U.S. Pat. No. 4,496,708, Dehm et al., issued Jan. 29, 1985, teaches water-soluble polyurethanes having hydrophilic polyether backbones and pendant monovalent hydrophobic groups to result in a hydrophilic/lipophilic balance of between about 14 and about 19.5. U.S. Pat. No. 4,426,485, Hoy et al., issued Jan. 17, 1984, discloses a water-soluble thermoplastic organic polymer having segments of bunched monovalent hydrophobic groups. U.S. Pat. No. 4,415,701, Bauer, issued Nov. 15, 1983, discloses copolymers containing a monoepoxide and a dioxolane.

The most preferred primary thickener materials for use in the present invention are disclosed in U.S. Pat. No. 4,228,277, Landoll, issued Oct. 14, 1980, which is incorporated herein by reference. The materials disclosed therein are thickeners comprising a nonionic long chain alkylated cellulose ether.

The cellulose ethers have a sufficient degree of nonionic substitution selected from the group consisting of methyl, hydroxyethyl and hydroxypropyl to cause them to be water-soluble. The cellulose ethers are further substituted with a hydrocarbon radical having about 10 to 22 carbon atoms in an amount between about b 0.2 weight percent and the amount which renders said cellulose ether less than 1%, by weight, soluble in water. The cellulose ether to be modified is preferably one of low to medium molecular weight, i.e., less than about 800,000 and preferably between about 20,000 and 700,000 (about 75 to 2500 D.P.)

The Landoll patent teaches that any nonionic water-soluble cellulose ether can be employed as the cellulose ether substrate. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The preferred cellulose ether substrate is hydroxyethyl cellulose (HEC) of about 50,000 to 700,000 molecular weight. Hydroxyethyl cellulose of this molecular weight level is the most hydrophilic of the materials contemplated. It can thus be modified to a greater extend than can other water-soluble cellulose ether substrates before insolubility is achieved. Accordingly, control of the modification process and control of the properties of the modified product can be more precise with this substrate. Hydrophilicity of the most commonly used nonionic cellulose ethers varies in the general direction: hydroxyethyl→hydroxypropyl→hydroxypropylmethyl→methyl.

The long chain alkyl modifier can be attached to the cellulose ether substrate via an ether, ester or urethane linkage. The ether linkage is preferred.

Although the materials taught in Landoll are referred to as being "long chain alkyl group modified", it will be recognized that except in the case where modification is effected with an alkyl halide, the modifier is not a simple long chain alkyl group. The group is actually an alphahydroxyalkyl radical in the case of an epoxide, a urethane radical in the case of an isocyanate, or an acyl radical in the case of an acid or acyl chloride. Nonetheless, the terminology "long chain alkyl group" is used since the size and effect of the hydrocarbon portion of the modifying molecule completely obscure any noticeable effect from the connecting group. Properties are not significantly different from those of the product modified with the simple long chain alkyl group.

Methods for making these modified cellulose ethers are taught in Landoll ('277) at column 2, lines 36-65.

These materials have been found to be particularly desirable for use in the vehicle systems of the cosmetic compositions of the present invention. The materials are able to stabilize suspensions of dispersed phases, and when used with the additional components in the vehicle systems of the present invention, they produce rheologically thick products which lack the slimy feel characteristic of most polymeric thickeners.

One commercially available material which meets these requirements is NATROSOL PLUS Grade 330, hydrophobically modified hydroxyethylcellulose available from Aqualon Company, Wilmington, Del. This material has a $C_{16}$ alkyl substitution of about 0.4% to about 0.8% by weight. The hydroxyethyl molar substitution for this material is from about 3.0 to about 3.7. The average molecular weight for the water-soluble cellulose prior to modification is approximately 300,000.

Another material of this type is sold under the trade name NATROSOL PLUS CS Grade D-67, by Aqualon Company, Wilmington, Del. This material has a $C_{16}$ alkyl substitution of from about 0.50% to about 0.95%, by weight. The hydroxyethyl molar substitution for this material is from about 2.3 to about 3.3, and may be as high as about 3.7. The average molecular weight for the water-soluble cellulose prior to modification is approximately 700,000.

The primary thickener component is present in the cosmetic compositions of the present invention at from about 0.1% to about 10.0%, preferably from about 0.2% to about 5.0%.

It is important that the primary thickener be well-hydrated and dispersed in the compositions of the present invention.

Water-Soluble Surfactant

The present vehicle systems further comprise, as a second essential component, a water-soluble surfactant having a molecular weight of less than about 20,000. By "water-soluble surfactant" is meant surfactant materials which form clear isotropic solutions when dissolved in water at 0.2 weight percent at ambient conditions.

Nonlimiting examples of water-soluble surfactants which can be used in the vehicle systems of the compositions of the present invention can be selected from water-soluble anionic, nonionic, cationic, zwitterionic and amphoteric surfactants.

Synthetic anionic surfactants include alkyl and alkyl ether sulfates. These materials have the respective formulae $ROSO_3M$ and $RO(C_2H_4O)_xSO_3M$, wherein R is alkyl or alkenyl of from about 10 to about 20 carbon atoms, x if 1 to 10, and M is a water-soluble cation such as ammonium, sodium, potassium and triethanolamine. The alkyl ether sulfates useful in the present invention are condensation products of ethylene oxide and monohydric alcohols having from about 10 to about 20 carbon atoms. Preferably, R has from about 12 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species, having, for example, an average of 3 moles of ethylene oxide per mole of alcohol, is sulfated and neutralized.

Specific examples of alkyl ether sulfates which can be used in the present invention are sodium coconut alkyl triethylene glycol ether sulfate; sodium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds; from about 3 to about 30% by weight of compounds having a degree of ethoxylation of 0; from about 45 to about 90% by weight of compounds having a degree of ethoxylation of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic surfactants are the water-soluble salts of the organic, sulfuric acid reaction products of the general formula:

$$R_1 - SO_3 - M$$

wherein $R_1$ is chosen from the group consisting of a straight or branched chain, saturated aliphatic hydrocarbon radical having from about 8 to about 24, preferably about 8 to about 14, carbon atoms; and M is a cation. Important examples are the salts of an organic sulfuric acid reaction product of a hydrocarbon of the methane series, including iso-, neo-, ineso-, and n-parrafins, having about 8 to about 24 carbon atoms, preferably about 8 to about 14 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Still other anionic synthetic surfactants include the class designated as succinamates. This class includes such surface active agents as disodium N-dodecylsulfosuccinamate; tetrasodium N-(1,2-dicarboxyethyl)-N-dodecylsulfosuccinamate; diamyl ester of sodium sulfosuccinic acid; dihexyl ester of sodium sulfosuccinic acid.

Other suitable anionic surfactants utilizable herein are olefin sulfonates having about 12 to about 24 carbon atoms. The term "olefin sulfonates" is used herein to means compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having about 12 to about 24 carbon atoms, preferably about 12 to about 16 carbon atoms. Preferably, they are straight chain olefins. Examples of suitable 1-olefins include 1-dodecene; 1-tetradecene; and 1-hexadecene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880, Pflaumer and Kessler, issued July 25, 1967, incorporated herein by reference.

Another class of anionic organic surfactants are the β-alkyloxy alkane sulfonates. These compounds have the following formula:

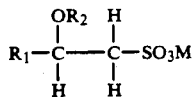

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Many additional nonsoap synthetic anionic surfactants are described in *McCutcheon's, Detergents and Emulsifiers*, 1984 Annual, published by Allured Publishing Corporation, which is incorporated herein by reference. Also U.S. Pat. No. 3,929,678, Laughlin et al., issued Dec. 30, 1975, discloses many other anionic as well as other surfactant types and is incorporated herein by reference.

Nonionic surfactants, can be broadly defined as compounds containing a hydrophobic moiety and a nonionic hydrophilic moiety. Examples of the hydrophobic moiety can be alkyl, alkyl aromatic, dialkyl siloxane, polyoxyalkylene, and fluoro-substituted alkyls. Examples of hydrophilic moieties are polyoxyalkylenes, phosphine oxides, sulfoxides, amine oxides, and amides. Examples of preferred classes of nonionic surfactants are:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000 are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond, Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphospine oxide, tetradecyldiethylphosphine oxide, dodecyldipropylphospine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one shot chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: 2-ketotridecyl methyl sulfoxide, 3,6,9-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

7. Silicone copolyols which may be polyalkylene oxide modified dimethylpolysiloxanes of the following formulae:

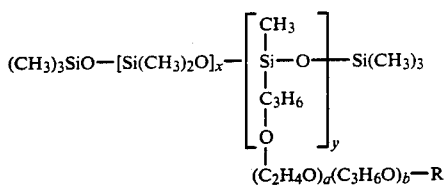

and

and

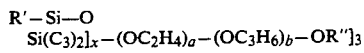

wherein R is hydrogen, an alkyl group having from 1 to about 12 carbon atoms, an alkoxy group having from 1 to about 6 carbon atoms or a hydroxyl group; R' and R" are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30.

Dimethicone copolyols among those useful herein are disclosed in the following patent documents, all incorporated by reference herein: U.S. Pat. No. 4,122,029, Gee et al., issued Oct. 24, 1978; U.S. Pat. No. 4,265,878, Keil, issued May 5, 1981; and U.S. Pat. No. 4,421,769, Dixon et al., issued Dec. 20, 1983. Such dimethicone copolyol materials are also disclosed, in hair compositions, in British Patent Application 2,066,659, Abe, published July 15, 1981 (incorporated by reference herein) and Canadian Patent 727,588, Kuehns, issued Feb. 8, 1966 (incorporated by reference herein). Commercially available dimethicone copolyols, which can be used herein, include Silwet Surface Active Copolymers (manufactured by the Union Carbide Corporation); and Dow Corning Silicone Surfactants (manufactured by the DOW Corning Corporation).

8. Amdie surfactants which include the ammonia, monoethanol, diethanol, other alkanol, and ethoxylated amides of fatty acids having an acyl moiety of from about 8 to about 22 carbon atoms and represented by the general formula

wherein $R_1$ is a saturated or unsaturated, aliphatic hydrocarbon radical having from 7 to 21, preferably from 11 to 17 carbon atoms; $R_2$ represents a $C_{1-4}$ alkalene group; and m is 1, 2, or 3, preferably 1; and $R_3$ can be H or $(C_2H_4O)_x$ where x is from 0 to 50. Specific examples of said amides are diethanol dodecyl fatty acid amide and PEG-5 lauramide. These acyl moieties may be derived from naturally occurring glycerides, e.g., coconut oil, palm oil, soybean oil and tallow, but can be derived synthetically, e.g., by the oxidation of petroleum, or by hydrogenation of carbon monoxide by the Fischer-Tropsch process. The ethoxylated amides and diethanolamides of $C_{18-22}$ fatty acids are preferred.

Cationic surfactants useful in vehicle systems of the compositions of the present invention, contain amino or quaternary ammonium hydrophilic moieties which are positively charged when dissolved in the aqueous composition of the present invention. Cationic surfactants among those useful herein are disclosed in the following documents, all incorporated by reference herein: M.C. Publishing Co., McCutcheon's, Detergents Emulsifiers, (North American Edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued June 7, 1983.

Among the quaternary ammonium-containing cationic surfactant materials useful herein are water-soluble surfactants of the general formula:

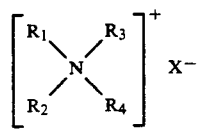

wherein $R_1$–$R_4$ can independently be selected from an aliphatic group of from about 1 to about 22 carbon atoms, hydroxyalkyl, $C_1$–$C_3$ alkyl, polyalkoxy, or an aromatic, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

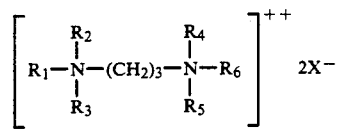

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include monoalkyltrimethyl ammonium chloride, wherein the alkyl groups having from about 12 to about 22 carbon atoms and are derived from long-chain fatty acids, such as hydrogenated tallow fatty acid (tallow fatty acids yield quaternary compounds wherein $R_1$ and $R_2$ have predominantly from 16 to 18 carbon atoms). Examples of quaternary ammonium salts useful in the present invention include cetyl trimethyl ammonium chloride, stearyl trihydroxyethyl ammonium chloride, cetyl pyridinium chloride, and behenyl trimethyl ammonium chloride.

primary, secondary, tertiary and ethoxylated fatty amines and their salts are also preferred cationic surfactant materials for use herein. The alkyl groups of such amines preferably have from about 12 to about 22 carbon atoms, and may be substituted or unsubstituted. Secondary and tertiary amines are preferred, tertiary amines are particularly preferred. Such amines, useful herein, include lauramido propyl dimethyl amine, diethyl amino ethyl lauramide, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and PEG-5 lauramide, Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and lauramidopropyl dimethylamine citrate. Cationic amine surfactants included among those useful int he present invention are disclosed in U.S. Pat. No. 4,275,055, Nachtigal, et al., issued June 23, 1981, incorporated by reference herein.

Zwitterionic surfactants are exemplified by those which can be broadly described as derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. A general formula for these compounds is:

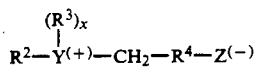

wherein $R^2$ contain an alkyl, alkenyl, or hydroxy alkyl radical of from about 8 to about 18 carbon atoms, from 0 to about 10 ethylene oxide moieties and from 0 to about 1 glyceryl moiety; is selected from the group consisting of nitrogen, phosphorus, and sulfur atoms; $R^3$ is an alkyl or monohydroxyalkyl group containing about 1 to about 3 carbon atoms; X is 1 when is a sulfur atom, and 2 when is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionics such as betaines are also useful in the present invention. Examples of betaines useful herein include the high alkyl betaines, such as coco dimethylcarboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gammacarboxypropyl betaine, and lauryl bis-(2-hydroxypropyl)alphacarboxyethyl betaine. The sulfobetaines may be represented by coco dimethyl sulfopropyl betaine, cetyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCON(C_2)_3$ radical is attached to the nitrogen atom of the betaine are also useful in this invention.

Examples of amphoteric surfactants which can be used in the vehicle systems of the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Examples of particularly preferred water-soluble surfactant materials for use in the present vehicle systems are cetyl betaine, ammonium lauryl sulfate, ammonium laureth sulfate, and cetyl trimethyl ammonium chloride, and mixtures thereof.

The water-soluble surfactant is used with the primary thickener of the present invention at from about 0.02% to about 0.03%, preferably from about 0.05% to about 0.30%, most preferably from about 0.05% to about 0.20%, of the composition. The water-soluble surfactant level is kept low because higher levels of water-soluble surfactants interfere with the primary thickener and produce compositions with much less desirable rheologies.

Solvent

A third essential component in the vehicle systems of the present invention is a solvent which is compatible with the other components in the present compositions. Generally the solvent will comprise water or a water-lower alkanol mixture. The solvent is present in the compositions of the present invention at a level of from about 65% to about 99% by weight of the cosmetic composition.

The other components are dispersed or mixed in the solvent to provide an optimum thick rheology to the cosmetic compositions formulated therewith which mimics the gel-network rheology of typical hair conditioning compositions. This rheology is characterized by a shear stress of from 0 to about 50 pascal, over a shear rate range of 0.04 sec$^{-1}$ to 25 sec$^{-1}$. The rheology is measured using a Bohlin Rheometer VOR with the following cone and plate set-up: cone has a 2.5 degree angle, plate is 30 mm in diameter, the gap between the truncated cone and plate is set at 70 $\mu$m, and the toque bar used is 20.148 g-cm. The sample amount is 0.35 ml and the sample is syringed onto the center of the plate. The system used is as follows: there is no initial delay time, the strain delay time is 25 sec, the integration time is 5 sec, the sensitivity is set at 1 X, the shear sweep is up, the shear range is from about 0.0405 sec$^{-1}$ to 25.53 sec$^{-1}$ (shear No.=11 to 39), and the temperature is maintained constant between series at ambient temperature (20° C. to 25° C.).

Additional Thickener

The present vehicle systems can also comprise an additional thickening component, which comprises a water-soluble polymeric material, having a molecular weight greater than about 20,000. By "water-soluble polymer" is meant that the material will form substantially a clear solution in water at a 1% concentration at 25° C. and the material will increase the viscosity of the water. Examples of water-soluble polymers which may desirably be used as an additional thickening component in the present vehicle systems, are hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone K-120, dextrans, for example, Dextran purified crude Grade 2P, available from D&O Chemicals, carboxymethylcellulose, plant exudates such as acacia, ghatti, and tragacanth, seaweed extracts such as sodium alginate, propylene glycol alginate and sodium carrageenan, and Ucare JR-polymer (a cationic modified hydroxyethyl cellulose available from Union Carbide). preferred as the optional additional thickener for the present vehicle systems are natural polysaccharide materials. Examples of such materials are guar gum, locust bean gum, and xanthan gum. Also preferred as the additional thickener in the present compositions is hydroxyethyl cellulose, having a molecular weight of about 700,000. It is important that these polymer materials not contain cellulose as this may interfere with obtaining optimum product viscosities.

The additional thickening component, if present in the cosmetic compositions of the present invention, is at a level of from about 0.3% to about 5.0%, preferably from about 0.4% to about 3.0%.

It is important that these additional polymer materials be well-hydrated and dispersed in the present compositions.

Rheological Aid

The vehicle systems of the present invention preferably also contain a material which provides additional rheological benefits to the cosmetic compositions formulated therewith. These materials are chelating agents. In general, such materials include monodentate and multidentate agents. Specific examples of useful chelating agents include ethylenediaminetetraacetic acid (EDTA), and salts thereof, nitriloacetic acid (NTA) and salts thereof, hydroxyethyl ethylene diamine triacetic acid (EEDTA) and salts thereof, diethylene triamine pentaacetic acid (DTPA) and salts thereof, diethanolglycine (DEG) and salts thereof, ethanol diglycine (EDG) and salts thereof, citric acid and salts thereof, phosphoric acid and salts thereof. The most preferred of these is EDTA. The chelating agents tend to make the vehicle systems of the present invention smoother and less gelatinous in consistency.

If a chelating agent is present as a rheological aid in the compositions of the present invention it is present at a level of from about 0.05% to about 1.0%, preferably from about 0.05% to about 0.3%, of the composition.

Distributing Aid

An additional component in the vehicle systems of the present invention is a material which acts as a distributing aid for the composition. Such a material helps to distribute the cosmetic composition onto the hair or skin avoiding localized deposition of the active component onto the hair or skin. Without such a component in a composition, some active components in the composition would not be deposited and spread out as evenly, and hence, would not be quite as effective.

Distributing aid materials useful in the present invention are actually a subclass of the class of materials used as the optional water-soluble polymer additional thickener in the present invention. This subclass is defined as follows: water-soluble polymer materials having high molecular weight, i.e., greater than 1,000,000; and/or strong ionic character. By strong ionic character is means that the material conducts electricity at greater than 30 millivolts. This can be measured by evaluating conductance of a 1% solution of polymer in DRO (double reverse osmosis) water preserved with 0.03% Kathon CG (a preservative available from Rohm & Haas) using a calibrated Corning 130 p meter. The probes used are as follows. The reference electrode is an Orion Model 9001 single junction. The p electrode is an Orion Model 9161, silver-silver chloride. The probes are set ⅜ of an inch apart. The p meter is set to millivolt readings. The absolute measurement is recorded after 4 minutes immersion.

Examples of water-soluble polymer materials which meet these requirements and hence, can act as distributing aids in the present compositions, include xanthan gum; Dextran purified crude Grade 2P, available from DO Chemicals; carboxymethyl celluloses; for example, CMC's 4H1F, 4M6F, 7HF, 7M8SF, 7LF, 9H4F, 9M8, 12M8P, 16M31 (all available from Aqualon); plant exudates such as acacia, ghatti and tragacanth; seaweed extracts such as sodium alginate, propylene glycol alginate, and sodium carrageenan; high molecular weight hydroxyethylcelluloses, such as Natrosol 250 H and Natrosol 250 R (available from Aqualon); and pectin.

Because the class of materials which may act as distributing aids in the present invention is a subset of the optional water-soluble polymer additional thickener, the materials in this subclass may be used to provide both benefits to the composition. For example, xanthan gum is a water-soluble natural polysaccharide material which additionally has a high molecular weight. Hence, this material could be used by itself to provide both additional thickening benefits and distributing benefits. However it may be necessary to use such materials at slightly higher levels to provide both benefits.

It is also possible to use two separate materials as the optional water-soluble polymer additional thickener and the distributing aid of the present invention. This would be done when the water-soluble polymer additional thickener was not a high molecular weight material or of strong ionic character. Locust bean gum is such a material. A distributing aid such as xanthan gum could be used with locust bean gum to provide the additional distributing benefits.

If a distributing aid is present in the cosmetic compositions of the present invention, it should be present at a level of from about 0.02% to about 2.5%, preferably from about 0.05% to about 1.0%, of the cosmetic composition. If the distributing aid is bifunctional, i.e., acting as both the optional additional thickener and the distributing aid it should be present at a level of from about 0.2% to about 5.0% of the composition.

A distributing aid is particularly useful in hair care compositions of the present invention, especially rinse-off hair conditioners. The distributing aid helps to spread same hair conditioning components evenly over the hair.

The present vehicle systems and cosmetic compositions formulated therewith must comprise no more than about 1%, preferably no more than about 0.5%, total of water-soluble surfactant materials. High levels of these materials are not compatible with the vehicle systems of the present composition. High levels of these materials destroy the unique desirable rheology that is the object of the present invention. Examples of specific water-soluble surfactant materials that can be particularly harmful to the present vehicle systems at high levels are alkyl sulfates and ethoxylated alkyl sulfates, such as ammonium lauryl sulfate; amphoteric surfactants which are derivatives of aliphatic secondary and tertiary amines; nonionic surfactants produced by the condensation of alkylene oxide groups with an organic hydrophilic compound, such as laureth-23 (sold under the trademark Brij 35 by ICI Americas); and high alyl betaines, sulfo betaines, amido betaines and amido sulfobetaines, such as cetyl betaine. Such materials are commonly used in hair shampoo compositions.

The present vehicle systems and cosmetic compositions formulated therewith are also preferably substantially free of fatty alcohol materials, such as stearyl-, cetyl-, myristyl-, behenyl-, lauryl-, and oleyl alcohols. By "substantially free of fatty alcohol materials" is meant that the compositions of the present invention comprise no more than about 1% of these materials. These materials are commonly used in vehicle systems for hair conditioner products. However, these materials are undesirable because they tend to deposit on the hair and leave the hair feeling dirty after use. These materials are not required and are not desirable in the present vehicle systems, as they are thickened with alternative materials which do not deposit on hair.

The present vehicle systems can be used in essentially any cosmetic products having a thick gel-network type rheology and which are used to deliver some active component onto the hair or skin. Such compositions would include skin moisturizing lotions, sunscreen compositions, and skin cleansing compositions. However, cosmetic compositions most desirably used with the present vehicle systems are hair care products, especially rinse-off hair care products where some active hair care component is to be deposited onto the hair but the vehicle carrying that component is desirably rinsed off the hair with little or not deposition of the vehicle material onto the hair.

Generally, the present vehicle systems will not be useful in typical shampoo compositions since these compositions contain high levels of water-soluble surfactants, which, as discussed supra, are incompatible with the present vehicle systems. However, the present vehicle systems are useful in typical hair coloring compositions, hair tonic or gel compositions, hair mousse compositions, and especially hair conditioning compositions.

Active Cosmetic Component

The cosmetic compositions of the present invention generally will comprise some active component which provides some benefit to the hair or skin. Such materials may include moisturizing agents, sunscreen agents, cleaning agents (that are compatible with the present vehicle systems), and especially hair conditioning agents, hair styling agents, antidandruff agents, hair growth promoters, hair dyes and pigments, or perfumes.

A wide variety of conventional sunscreening agents are suitable for use in the cosmetic compositions of the present invention. Segarin et al., at Chapter VIII, pages 189 et seq., of Cosmetics Science and Technology, disclose numerous suitable agents. Specific suitable sunscreening agents include, for example: p-aminobenzoic acid, its salts and its derivatives; anthranilates; salicylates; cinnamic acid derivatives; dihydroxycinnamic acid derivatives; trihydroxycinnamic acid derivatives; hydrocarbons; dibenzalacetone and benzalacetophenone; naphtholsulfonates; dihydroxy-naphtholic acid and its salts; coumarin derivatives; diazoles; quinine salts; quinoline derivatives; hydroxy- or methoxy-substituted benzophenones; uric and vilouric acids; tannic acid and its derivatives; hydroquinone; and benzophenones.

Of these, 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 1,1-dihydroxy-4-methoxybenzophenone, ethyl-4-[bis(hydroxypropyl)]-aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid 2-(p-dimethylaminophenyl)-5-sulfonicbanzoxazoic acid, and mixtures of these compounds, are particularly useful.

Examples of antidandruff aids suitable for use with the vehicle systems of the present invention include zinc pyrithione, sulphur, and selenium sulfide. An example of a hair growth promoter suitable for use with the vehicle systems of the present invention is Minoxidil (6-amino-1,2-dihydro-1-hydroxy-2-imino-4-piperidinopyrimidine) available from Upjohn. Hair oxidizing (bleaching) agents, such as hydrogen peroxide, perborate and persulfate salts, and hair reducing agents such as thioglycolates may also be used.

Examples of hair conditioning materials suitable for use in the vehicle systems of the present invention are volatile liquid hydrocarbon or silicone agents.

These materials preferably have a boiling point in the range of about 99° C. to about 260° C. and have a solubility in water of less than about 0.1%. The hydrocarbons may be either straight or branched chain and may contain from about 10 to about 16, preferably from about 12 to about 16 carbon atoms. Examples of suitable hydrocarbons are decane, dodecane, tetradecane, tridecane and mixtures thereof.

The volatile silicones useful as the active hair treating component in the compositions of the present invention may be either a cyclic or a linear polydimethylsiloxane. The number of silicon atoms int he cyclic silicones is preferably from about 3 to about 7, more preferably 4 or 5.

The general formula for such silicones is

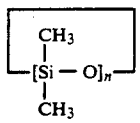

wherein n=3-7. The linear polydimethylsiloxanes have from about 3 to 9 silicon atoms and have the general formula:

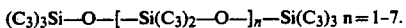

Silicones of the above type, both cyclic and linear, are available from Dow Corning Corporation, Dow Croning 344, 345 and 200 fluids; Union Carbide, Silicone 7202 and Silicone 7158; and Stauffer Chemical, SWS-03314.

The linear volatile silicones generally have viscosities of less than about 5 centipose at 25° C. while the cyclic materials have viscosities less than about 10 centipoise. "Volatile" means that the material has a measurable vapor pressure. A description of volatile silicones is found in Todd and Byers, "Volatile Silicone Fluids for Cosmetics", Cosmetics and Toiletries, Vol. 91, January 1976, pp. 17-32, incorporated herein by reference.

The volatile agent may be present in the compositions of this invention at a level of from about 1% to about 20%, preferably from about 2% to about 15%. The volatile silicones are the preferred volatile agents.

Nonvolatile silicone fluids are also useful as the active hair care component in the compositions of the present invention. Examples of such materials include polydimethylsiloxane gums, aminosilicones and phenylsilicones. More specifically, materials such as polyalkyl or polyaryl siloxanes with the following structure:

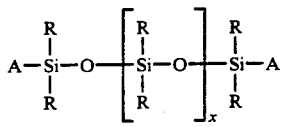

wherein R is alkyl or aryl, and x is an integer from about 7 to about 8,000 may be used. A represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

Suitable methods for preparing these silicone materials are disclosed in U.S. pat. Nos. 2,826,551 and 3,964,500 and references cited therein. Silicones useful int he present invention are also commercially available. Suitable examples include Viscasil, a trademark of the General Electric Company and silicones offered by Dow Croning Corporation and by SWS Silicones, a division of Stauffer Chemical Company.

Other useful silicone materials include materials of the formula:

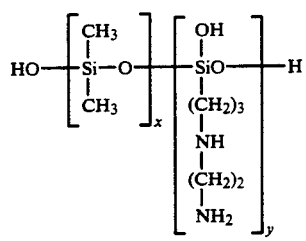

(I)

in which x and y are integers which depend on the molecular weight, the average molecular weight being approximately between 5,000 and 10,000. This polymer is also known as "amodimethicone".

Other silicone cationic polymers which can be used in the present composition correspond to the formula:

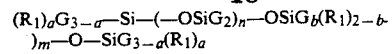

in which G is chosen from the group consisting of hydrogen, phenyl, O, $C_1$-$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_qH_{2q}L$ in which q is an integer from 2 to 8 and L is chosen from the groups

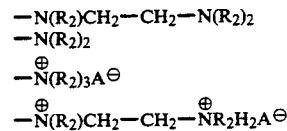

in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

These compounds are described in greater detail in European patent Application EP 95,238. An especially preferred polymer corresponding to this formula is the polymer known as "trimethylsilylamodimethicone" of formula:

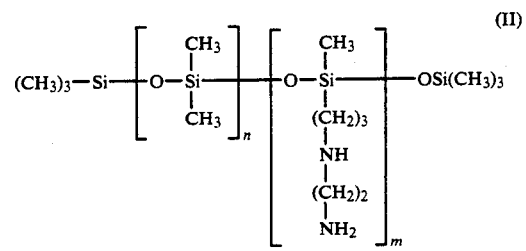

Compositions of the present invention may comprise up to about 1.0% of a trimethylsilyl amodimethicone silicone conditioning material.

Other silicone cationic polymers which can be used in the present compositions correspond to the formula:

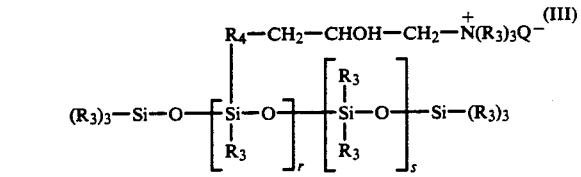

in which $R_3$ denotes a monovalent hydrocarbon radical having from 1 to 18 carbon atoms, and more especially an alkyl or alkenyl radical such a methyl; $R_4$ denotes a hydrocarbon radical such as, preferably a $C_1$-$C_{18}$ alkylene radical or a $C_1$-$C_{18}$, and preferably $C_1$-$C_8$, alkyleneoxy radical;

$Q^-$ is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

Silicone conditioning agents are used in the present compositions at levels of from about 0.1% to about 18%, preferably from about 0.5% to about 15%.

Preferred silicone conditioning agents for use in the present compositions comprise combinations of volatile silicone fluids having viscosities of less than about 10 centipoise, and from about 0.015% to about 9.0%, preferably from about 0.5% to about 2.0%, of silicone gums having viscosities of greater than about 1,000,000 centipoise, at ratios of volatile fluid to gum of from about b 90:10 to about 10:90, perferably from about 85:15 to about 50:50.

Alternative preferably non-volatile silicone materials for use in the present invention comprise non-volatile silicone fluids having viscosities of less than about 100,000 cP (centipoise), and from about 0.015% to about 9.0%, preferably from about 0.5% to about 2.0%, of silicone gums having viscosities greater than about 1,000,000 cP, especially polydimethylsiloxane gums and polyphenylmethylsiloxane gums, at ratios of non-volatile fluid to gum of from about 70:30 to about 30:70, preferably from about 60:40 to about 40:60.

Other preferred active hair care materials for use with the vehicle systems of the present invention are silicone polymer materials which provide both style retention and conditioning benefits to the hair. Although silicone fluids are useful in the present compositions, preferred silicone polymers are rigid silicone polymers. Such materials are described in U.S. Pat. No. 4,902,499, Bolich et al., issued Feb. 20, 1990, and U.S. Pat. No. 4,906,459, Bolich et al., issued Mar. 6, 1990.

Some examples of such materials include, but are not limited to, filler reinforced polydimethyl siloxane gums including those having end groups such as hydroxyl; cross linked siloxanes, such as organic substituted silicone elastomers; organic substituted siloxane gums, including those having end groups such as hydroxyl; resin reinforced siloxanes; and cross linked siloxane polymers.

The rigid silicone polymers useful in the present invention have complex viscosities of at least $2 \times 10^5$ poise (P), preferably about $1 \times 10^7$ poise, where complex viscosity is measured by subjecting a sample to oscillatory shear at a fixed frequency of 0.1 rad/sec at 25° C. using a Rheometric Fluids Spectrometer ® measuring films having a thickness of about 1 millimeter. The resulting viscous and elastic force responses are combined to determine the complex modulus which is divided by the imposed frequency to compute the complex viscosity.

A preferred siloxane gum useful in the present invention is a diphenyl-dimethyl polysiloxane gum having a molecular weight of at least about 500,000, and must be diphenyl substituted to the extent of 3% or more, preferably at least about 5%.

The siloxane gums may also be filler reinforced to provide additional rigidity. Silica is the preferred filler. Generally such reinforced gums comprise up to about 15-20% silica.

Silicone elastomers useful in the compositions of the present invention are the materials described in U.S. Pat. No. 4,221,688, Johnson et al., issued Sept. 9, 1980, incorporated herein by reference. The actual material described int he patent and what can be put into the present compositions is an aqueous emulsion which dries to form an elastomer upon removal of the water.

The silicone emulsion has a continuous water phase in which there is a dispersed phase which comprises an anionically stabilized hydroxylated polyorganosiloxane, a colloidal silica and a catalyst. The pH of the emulsion should be in the range of from about 9 to about 11.5, preferably from about 10.5 to about 11.2. The solids content of the emulsion is generally from about 20% to about 60%, preferably from about 30% to about 50%. The amount of colloidal silica present for each 100 parts by weight of the polydiorganosiloxane is from 1 to 150 parts. On the same basis the amount of a diorganotindicarboxylate (e.g., dioctyl tindilaurate) catalyst is from 0.1 to 2 parts. The elastomer emulsion is used in an amount of from about 0.1% to about 5%, preferably from about 0.5% to about 4%, of the total composition.

Silicone resins useful in the present compositions are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. A preferred resin is one offered by General Electric as GE SR545. This resin is provided as a solution in toluene which is stripped prior to the resin's use.

Other rigid silicone polymers of use herein are those siloxanes which have been sparingly crosslinked but are still soluble in solvents such as cyclomethicone. Precursors for the rigid material can be any high molecular weight polydimethyl siloxanes, polydimethyl siloxanes containing vinyl groups and other siloxanes. Methods of crosslinking include heat curing with organic peroxides such as dibenzoyl peroxide and di-t-butyl peroxide, heat vulcanization with sulfur, and high-energy radiation.

Generally, the silicone gum, if used in the present compositions, is dissolved in a volatile carrier, or mixtures thereof, prior to incorporation into the hair care compositions. Preferably, the volatile carrier is present in the hair care composition at from about 0.1% to about 20% of the hair care composition. These materials can comprise the volatile liquid hydrocarbon or silicone fluids described supra.

Preferably, the rigid silicone polymer and carrier comprises from about 0.1% to about 2.5% of a polydimethylsiloxane gum; from about 0.02% to about 0.7% of fumed silica, and from about 0.4% to about 18% of a volatile silicone carrier.

Alternative hair conditioning materials may be used in the present compositions. Such materials include cationic surfactant materials which are well known as conditioning agents. Preferred cationic surfactants for use as hair conditioning agents in the present compositions are quaternary ammonium-containing cationic surfactant materials. If such a material is included in the present compositions it will be present at levels up to about 2.5%, preferably at from about 0.5% to about 2.0%, by weight of the composition. The preferred quaternary ammonium-containing cationic surfactant for use herein is di(hydrogenated) tallow dimethyl ammonium chloride.

Alternative cationic water-insoluble surfactant hair conditioning agents that may be used in the present compositions are salts of primary, secondary, and tertiary fatty amines. The preferred of these materials is stearamide propyl dimethyl amine. A commercially available material is sold under the trade name Lexamine ® by Inolex Company. Preferably, up to about 1% of such materials may be used in the present compositions to provide conditioning benefits.

Hydrolyzed animal protein hair conditioning agents may also be included in the present compositions. Such materials are present in the compositions at levels of from about 0.1% to about 1.5%. An example of a commercially available material is sold under the trade name Crotein Q ® from Croda, Inc.

Fatty alcohols are known hair conditioning agents and may be included in the present compositions. However, as described supra such materials tend to deposit on hair and leave hair feeling dirty after use. Hence, fatty alcohol materials are not included in the compositions of the present invention at levels greater than about 1%.

Combinations of the aforementioned conditioning agents may also be used in the present compositions.

Highly preferred active hair care materials for use with the vehicle systems of the present invention are hair holding/styling polymers. Highly preferred examples of such materials are the silicone-containing copolymers as described in concurrently filed patent applications: Ser. No. 390,559, Torgerson, Bolich and Garbe, filed Aug. 7, 1989, "now abandoned, which is the parent application of U.S. Ser. No. 07/505,760 filed Apr. 6, 1990, now abandoned, which is the parent application of U.S. Ser. No. 07/758,320, filed Aug. 19, 1991" between "Aug. 7, 1989"; and Ser. No. 390,568, Bolich and Torgerson, filed Aug. 7, 1989, now abandoned, which is the parent application of U.S. Ser. No. 07/505,755, filed Apr. 6, 1990, now abandoned, which is the parent application of U.S. Ser. No. 07/758,320, filed Aug. 19, 1991, both of which are incorporated by reference herein. Such polymers should have a weight average molecular weight of from about 10,000 to about 1,000,000 and preferably, have a Tg of at least about −20° C. As used herein, the abbreviation "Tg" refers to the glass transition temperature of the non-silicone backbone, and the abbreviation "Tm" refers to the crystalline melting point of the non-silicone backbone, if such a transition exists for a given polymer.

Preferred polymers comprise a vinyl polymeric backbone having a Tg or a Tm above about −20° C. and, grafted to the backbone, a polydimethylsiloxane macromer having a weight average molecular weight of from about 1,000 to about 50,000, preferably from about 5,000 to about 40,000, most preferably about 20,000. The polymer is such that when it is formulated into the finished hair care composition, when dried, the polymer phase separates into a discontinuous phase which includes the polydimethylsiloxane macromer and a continuous phase which includes the backbone. It is believed that this phase separation property provides a specific orientation of the polymer on hair which results in the desired hair conditioning and setting benefits.

In its broadest aspect, the copolymers utilized in the present application comprise C monomers together with monomers selected from the group consisting of A monomers, B monomers, and mixtures thereof. These copolymers contain at least A or B monomers together with C monomers, and preferred copolymers contain A, B and C monomers.

Examples of useful copolymers and how they are made are described in detail in U.S. Pat. No. 4,693,935, Mazurek, issued Sept. 15, 1987, and U.S. Pat. No. 4,728,571, Blemens et al., issued Mar. 1, 1988, both of which are incorporated herein by reference. These copolymers are comprised of monomers A, C and, optionally, B, which are defined as follows. A, when used, is at least one free radically polymerizable vinyl monomer or monomers. B, when used, comprises at least one reinforcing monomer copolymerizable with A and is selected from the group consisting of polar monomers and macromers having a Tg or a Tm above about −20° C. When used, B may be up to about 98%, preferably up to about 80%, more preferably up to about 20%, of the total monomers in the copolymer. Monomer C comprises from about 0.01% to about 50.0% of the total monomers in the copolymer.

Representative examples of A monomers are acrylic or methacrylic acid esters of $C_1$–$C_{18}$ alcohols, such as methanol, ethanol, 1-propanol, 2-propanol, 1l-butanol, 2l-methyl-1l-propanol, 1-pentanol, 2-pentanol, 3l-pentanol, 2-methyl-1l-butanol, 1l-methyl-1l-butanol, 3-methyl-1-butanol, 1-methyl-1l-pentanol, 2-methyl-1-pentanol, 3l-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5l-trimethyl-1-hexanol, 1-decanol, 1-dodecanol, 1-hexadecanol, 1-octadecanol, and the like, the alcohols having from about 1–18 carbon atoms with the average number of carbon atoms being from about 4–12; styrene; vinyl acetate; vinyl chloride; vinylidene chloride; acrylonitrile; alpha-methylstyrene; t-butylstyrene; butadiene; cyclohexadiene; ethylene; propylene; vinyl toluene; and mixtures thereof. Preferred A monomers include n-butyl methacrylate, isobutyl methacrylate, 2-ethylhexyl methacrylate, methyl methacrylate, t-butylacrylate, and t-butylmethacrylate, and mixtures thereof.

Representative examples of B monomers include acrylic acid, methacrylic acid, N,N-dimethylacrylamide, dimmethylaminoethyl methacrylate, quaternized dimethylaminoethyl methacrylate, methacrylonitrile, polystyrene macromer, methacrylamide, maleic anhydride and its half esters, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, acylactones, 2-ethyl-2l-oxazoline, vinyl pyridine, vinyl imidazole, other polar vinyl heterocyclics, styrene sulfonate, and mixtures thereof. Preferred B monomers include acrylic acid, N,N-dimethylacrylamide, dimethylaminoethyl methacrylate, quaternized dimethylaminoethyl methacrylate, vinyl pyrrolidone, and mixtures thereof.

The C monomer has the general formula:

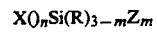

$$XO_nSi(R)_{3-m}Z_m$$

wherein X is a vinyl group copolymerizable with the A and B monomers; Y is a divalent linking group; R is a hydrogen, lower alkyl, aryl or alkoxy; Z is a monovalent siloxane polymeric moiety having a number average molecular weight of at least about 500, is essentially unreactive under copolymerization conditions and is pendant from the vinyl polymeric backbone, described above; n is 0 or 1; and m is an integer from 1 to 3. C has a weight average molecular weight of from about 1,000 to about 50,000, preferably from about 5,000 to about 40,000, most preferably from about 10,000 to about 20,000. Preferably, the C monomer has a formula selected from the following group:

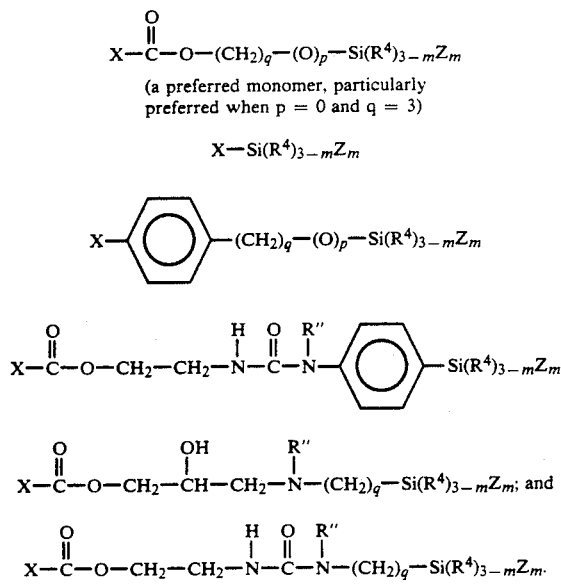

(a preferred monomer, particularly preferred when p = 0 and q = 3)

In those structures, m is 1, 2 or 3 (preferably m=1); p is 0 or 1; R" is alkyl or hydrogen; q is an integer from 2 to 6; s is an integer from 0 to 2; X is

$R^1$ is hydrogen or —COO (preferably $R^1$ is hydrogen); $R^2$ is hydrogen, methyl or —$C_2$COO (preferably $R^2$ is methyl); Z is

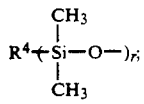

$R^4$ is alkyl, alkoxy, alkylamino, aryl, or hydroxyl (preferably $R^4$ is alkyl); and r is an integer from about 5 to about 700 (preferably r is about 250).

The preferred polymers useful in the present invention generally comprise from 0% to about 98% (preferably from about 5% to about 98%, more preferably from about 50% to about 90%) of monomer A, from 0% to about 98% (preferably from about 7.5% to about 80%) of monomer B, and from about 0.1% to bout 50% (preferably from about 0.5% to about 40%, most preferably from about 2% to about 25%) of monomer C. The combination of the A and B monomers preferably comprises from about 50.0% to about 99.9% (more preferably about 60% to about 99%, most preferably from about 75% to about 95%) of the polymer. The composition of any particular copolymer will help determine its formulational properties. For example, polymers which are soluble in an aqueous formulation preferably have the composition: from 0% to about 70% (preferably from about 5% to about 70%) monomer A, from about 30% to about 98% (preferably from about 3% to about 80%) monomer B, and from about 1% to about 40% monomer C. Polymers which are dispersible have the preferred composition: from 0% to about 70% (more preferably from about 5% to about 70%) monomer A, from about 20% to about 80% (more preferably from about 20% to about 60%) monomer B, and from about 1% to about 40% monomer C.

Particularly preferred polymers for use in the present invention include the following (the weight percents below refer to the amount of reactants added in the polymerization reaction, not necessarily the amount in the finished polymer):

acrylic acid/n-butylmethacrylate/polydimethylsiloxane (PDMS) macromer-20,000 molecular weight (10/70/20 w/w/w) (I)

N,N-dimethylacrylamide/isobutyl methacrylate/PDMS macromer 20,000 molecular weight (20/60/20 w/w/w) (II)

dimethylaminoethyl methacrylate/isobutyl methacrylate/2-ethylhexyl-methacrylate/PDMS macromer-20,000 molecular weight (25/40/1/20 w/w/w/w) (III)

dimethylacrylamide/PDMS macromer-20,000 molecular weight (80/20 w/w) (IV)

t-butylacrylate/t-butylmethacrylate/PDMS macromer-10,000 molecular weight (56/24/20 w/w/w) (V)

t-butylacrylate/PDMS macromer-10,000 molecular weight (80/20 w/w) (VI)

t-butylacrylate/N,N-dimethylacrylamide/PDMS macromer-10,000 molecular weight (70/10/20 w/w/w) (VII)

t-butylacrylate/acrylic acid/PDMS macromer-10,000 molecular weight (75/5/20 w/w/w) (VIII).

The particle size of the copolymer material of the present compositions may have some effect on performance in product. This, of course, will vary from copolymer to copolymer and from product to product.

The copolymers are preferably combined with a solvent for the copolymer prior to combination with the vehicle systems of the present invention.

The solvent selected must be able to dissolve or disperse the particular silicone copolymer being used. The nature and proportion of B monomer in the copolymer largely determines its polarity and solubility characteristics. The silicone copolymers can be designed, by appropriate combination of monomers, for formulation with a wide range of solvents. Suitable solvents for use in the present invention include, but are not limited to, water, lower alcohols (such as ethanol, isopropanol), hydroalcoholic mixtures, hydrocarbons (such as isobutane, hexane, decene, acetone), halogenated hydrocarbons (*such as Freon), linalool, hydrocarbon esters (such as ethyl acetate, dibutyl phthalate), volatile silicon derivatives, especially siloxanes (such as phenyl pentamethyl disiloxane, phenethyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), and mixtures thereof. Preferred solvents include water, ethanol, volatile silicon derivatives, and mixtures thereof.

The unique vehicle systems of the present invention provide superior performance vis a vis delivery of the active cosmetic component to the hair or skin. This is especially true in the case of hair care compositions. Lower levels of active components may be used in the hair care compositions of the present invention than are used in hair care compositions formulated with alternative thickening systems. These deposition benefits are especially noticeable in the case of silicone hair conditioning agents. The quantity and quality of silicone deposit from the present unique vehicle systems on hair results in enhanced hair conditioning.

These active cosmetic care materials are generally present at a level of from 0% to about 20%, preferably from about 0.1% to about 20%, by weight of the cosmetic composition. The 0% level reflects the situation when one of the vehicle components provides the hair care activity to the present compositions. For example, if the vehicle system comprises a water-soluble quaternary ammonium compound, this material will provide hair conditioning benefits as well. The level of the active cosmetic care material varies depending upon which active material is chosen, the particular cosmetic compositions to be formulated therewith, and the level of benefit desired.

Other optional components that can be added to the cosmetic compositions of the present invention do not provide any direct cosmetic care benefit but instead enhance the composition in some way. Examples of such materials are coloring agents, such as any of the FDC or DC dyes; opacifiers, pearlescent aids, such as ethylene glycol distearate or $TiO_2$ coated mica; pH modifiers, such as citric acid, succinic acid, phosphoric acid, sodium hydroxide, and sodium carbonate; preservatives, such as benzyl alcohol, ethyl paraben, propyl paraben, and imidazolidonyl urea; and antioxidants. Such agents generally are used individually at a level of from about 0.001% to about 10%, preferably from about 0.01% to about 5%, of the hair care composition.

The vehicle systems and cosmetic compositions of the present invention can be made using conventional formulation and mixing techniques. Methods of making various types of cosmetic compositions are described more specifically in the following examples.

The following examples illustrate the present invention. It will be appreciated that other modifications of the present invention within the skill of those in the cosmetic composition formulation art can be undertaken without departing from the spirit and scope of this invention.

All parts, percentages, and ratios herein are by weight unless otherwise specified.

EXAMPLE I

The following is a hair styling rinse composition representative of the present invention.

| Component | Weight % |
|---|---|
| Styling Agent | |
| Silicone Copolymer[1] | 3.00 |
| Phenylpentamethyl disiloxane | 9.00 |
| Hydroxypropylpentamethyl disiloxane | 6.00 |
| Premix | |
| Silicone Gum G.E. SE76[2] | 0.50 |
| Decamethyl cyclopentasiloxane | 4.00 |
| Main Mix | |
| Natrosol Plus CS Grade D-67[3] | 0.60 |
| Locust bean gum | 0.50 |
| EDTA, disodium salt | 0.15 |
| Cetyl trimethyl ammonium chloride | 0.04 |
| Glydant[4] | 0.40 |
| DRO $H_2O$ | q.s. to 100% |

[1]10/70/20 acrylic acid/n-butyl methacrylate/silicone macromer the macromer having a molecular weight of about 20,000, prepared in a manner similar to Example C-2c of U.S. Pat. No. 4,728,571, Clemens, issued March 1, 1988, polymer molecular weight about 300,000
[2]Commercially available from General Electric
[3]hydrophobically-modified hydroxyethyl cellulose having a $C_{16}$ alkyl substitution of from about 0.50% to about 0.95%, by weight, and a hydroxyethyl molar substitution of from about 2.3 to about 3.3, and where the average molecular weight of the hydroxyethylcellulose prior to substitution is approximately 700,000, commercially available from Aqualon Co.
[4]preservative commercially available from Glyco, Inc.

The composition is prepared as follows. The DRO water is heated to 190° F. The DTDMAC, EDTA, and silicone gum premix are added to the water with mixing for about 5 minutes. The Natrosol is added with mixing. The locust bean gum is added with mixing. The composition is then homogenized with a disperser, for example, a Gifford-Wood mill, for about 2 minutes. The batch is cooled to 150² F. and the styling agent premix, perfume and Glydant are added with mixing for about 10 minutes. The batch is cooled to ambient temperature and stored.

EXAMPLE II

The following is a hair pomade composition which is representative of the present invention.

| Component | Wt. % |
|---|---|
| Natrosol Plus CS Grade D-67[1] | 1.75 |
| Petroleum Jelly | 5.00 |
| Ammonium Lauryl Sulfate | 0.07 |
| Kathon CG | 0.04 |
| DRO Water | q.s. to 100% |

[1]Hydrophobically modified hydroxyethylcellulose available from Aqualon

The composition is prepared as follows. All of the ingredients are combined and mixed for about ½ hour at 60° C.

EXAMPLE III

The following is a skin lotion composition which is representative of the present invention.

| Component | Wt. % |
|---|---|
| Dimethicone, 350 CP | 0.50 |
| Mineral Oil | 0.50 |
| Glycerine | 3.00 |
| Natrosol Plus CS Grade D-67[1] | 1.20 |
| Cetyl Betaine | 0.10 |
| Kathon CG | 0.04 |
| DRO Water | q.s. to 100% |

[1]Hydrophobically modified hydroxyethylcellulose available from Aqualon

The composition is prepared as follows. All of the ingredients are combined and mixed for about ½ hour at 60° C.

EXAMPLE IV

The following is a hair styling conditioner composition which is representative of the present invention.

| Component | Wt. % |
|---|---|
| Disodium EDTA | 0.10 |
| Monosodium Phosphate | 0.08 |
| Disodium Phosphate | 0.02 |
| Lauryl Betaine | 0.08 |
| Natrosol Plus CS Grade D-67[1] | 1.50 |
| Glydant | 0.37 |
| DRO Water | q.s. to 100% |
| Styling Polymer Premix | |
| Styling Polymer[2] | 3.00 |
| Phenyl Pentamethyl Disiloxane | 4.95 |
| Octamethyl Cyclotetrasiloxane | 4.05 |
| Silicone Gum Premix | |
| G. E. SE 76[3] | 0.75 |
| Octamethyl Cyclotetrasiloxane | 4.25 |

[1]Hydrophobically modified hydroxyethylcellulose available from Aqualon
[2]Isobutylmethacrylate/2-ethylhexylmethacrylate/N,N-dimethyl-acrylamide copolymer 80/5/15
[3]Silicone Gum available from General Electric The composition is prepared as follows. The DRO water is heated to 190° F. The EDTA, tallow betaine, monosodium phosphate, and disodium phosphate are added and the composition is mixed for about 5 minutes. The silicone gum premix is added with mixing. The Natrosol is added with mixing. The composition is then homogenized with a disperser, for example, a Gifford-Wood Mill, for about 2 minutes. The batch is cooled to 150° F. The perfume and Glydant are then added with mixing for about 10 minutes. The batch is cooled to 80° F. and stored.

EXAMPLE V

The following is a styling rinse composition representative of the present invention.

| Component | Weight % |
|---|---|
| Styling Agent | |
| Silicone Copolymer[1] | 3.00 |
| Octamethyl cyclotetrasiloxane | 9.00 |
| Premix | |
| Silicone Gum GE SE76[2] | 0.50 |
| Decamethyl cyclopentosiloxane | 4.00 |
| Main Mix | |
| Natrosol Plus CS Grade D-67[3] | 1.25 |
| Cetyl Betaine | 0.04 |
| DTDMAC | 0.50 |
| Kathon CG[4] | 0.03 |
| Imidazole | 0.15 |
| Perfume | 0.10 |
| DRO H$_2$O | q.s. to 100% |

[1]80/20 t-butylacrylate/PDMS macromer, the macromer having a molecular weight of about 10,000, prepared in a manner similar to Example C-2b of U.S. Pat. No. 4,728,571, Clemens, issued March 1, 1988.
[2]commercially available from General Electric
[3]hydrophobically-modified hydroxyethyl cellulose commercially available from Aqualon Co.
[4]preservative commercially available from Rohm & Haas The composition is prepared as follows. The Styling Agent and Premix are blended separately by conventional means. The Main Mix is prepared by adding all the ingredients and heating to 95° C. for ½ hour with agitation. As the batch is cooled to about 60° C., the premix and Styling Agent mixes are added to the Main Mix with agitation and the batch is cooled to ambient temperature.

EXAMPLE VI

The following is a hair styling conditioner composition which is representative of the present invention.

| Ingredient | Wt. % |
|---|---|
| Premix: | |
| G. E. SE 76 Gum[1] | 0.80 |
| Cab-O-Sil HS-5[2] | 0.20 |
| Decamethylcyclopentasiloxane | 4.50 |
| Natrosol Plus CS Grade D-67[3] | 1.40 |
| Dehyquart SP[4] | 0.07 |
| Adogen 442 - 100P[5] | 0.50 |
| Glydant[6] | 0.37 |
| Disodium EDTA[7] | 0.15 |
| Disodium phosphate | 0.12 |
| Monosodium phosphate | 0.03 |
| PEG 600 | 0.50 |
| DRO H$_2$O | q.s. to 100% |

[1]Polydimethylsiloxane gum offered by General Electric
[2]Fumed silica offered by Cabot Corp.
[3]Hydrophobically modified hydroxyethyl cellulose available from Aqualon
[4]C$_{14}$-C$_{18}$ tallow trialkoxy ammonium chloride available from Henkel.
[5]Dihydrogenated tallow dimethyl ammonium chloride offered by Sherex Chemical Co.
[6]Preservative offered by Glyco, Inc.
[7]Ethylene diamine tetraacetic acid, disodium salt The composition is prepared as follows. The DRO water is heated to 190° F. The DTDMAC, Dehyquart S. P., Adogen 442-100P, EDTA, monosodium phosphate, disodium phosphate, and PEG 600 are added with mixing for about 5 minutes. The silicone premix is added with mixing. The Natrosol is added with mixing. The composition is then homogenized with a disperser, for example, a Gifford-Wood Mill, for about 2 minutes. The batch is cooled to 150° F. and the perfume and Glydant are added.

EXAMPLE VII

The following is a hair styling conditioner composition representative of the present invention.

| Ingredient | Wt. % |
|---|---|
| Premix 1: | |
| G. E. SE 76 Gum[1] | 0.80 |
| Cab-O-Sil HS-5[2] | 0.20 |
| Decamethylcyclopentasiloxane | 4.50 |
| Premix 2: | |
| G. E. SE 76 Gum | 0.50 |
| Decamethylcyclopentasiloxane | 2.80 |
| Natrosol Plus CS Grade D-67[3] | 1.39 |
| Laurylbenzyl dimethylammonium chloride | 0.05 |
| Adogen 442 - 100P[4] | 0.50 |
| Glydant[5] | 0.37 |
| Disodium phosphate | 0.12 |
| Monosodium phosphate | 0.03 |
| Disodium EDTA[6] | 0.15 |
| DRO H$_2$O | q.s. to 100% |

[1]Polydimethylsiloxane gum offered by General Electric
[2]Fumed silica offered by the Cabot Corp.
[3]Hydrophobically modified hydroxyethyl cellulose available from Aqualon
[4]Dihydrogenated tallow dimethyl ammonium chloride offered by Sherex Chemical Co.
[5]Preservative offered by Glyco, Inc.
[6]Ethylene diamine tetraacetic acid The composition is prepared as follows. The DRO water is first heated to 190° F. The lauryl benzyl dimethylammonium chloride, Adogen 441-100P, EDTA, mono- and di-sodium phosphate are added with mixing for about 5 minutes. The silicone premixes are added with mixing. The Natrosol is added with mixing. The composition is then homogenized with a disperser, e.g., a Gifford-Wood Mill, for about 2 minutes. The batch is cooled to 150° F. and the perfume and Glydant are added with mixing for about 10 minutes. The batch is cooled to ambient temperature and stored.

EXAMPLE VIII

The following is a hair styling conditioner composition which is representative of the present invention.

| Ingredient | Wt. % |
|---|---|
| Silicone Gum Premix: | |
| G. E. SE 76 Gum[1] | 0.10 |
| Decamethylcyclopentasiloxane | 0.60 |
| Natrosol Plus CS Grade D-67[2] | 1.50 |

-continued

| Ingredient | Wt. % |
| --- | --- |
| Cetyl Betaine | 0.10 |
| Adogen 442 - 100P[3] | 0.50 |
| Glydant[4] | 0.37 |
| Disodium EDTA[5] | 0.15 |
| Disodium phosphate | 0.12 |
| Monosodium phosphate | 0.03 |
| DRO H$_2$O | q.s. to 100% |

[1]Polydimethylsiloxane gum offered by General Electric
[2]Hydrophobically modified hydroxyethyl cellulose available from Aqualon
[3]Dihydrogenated tallow dimethyl ammonium chloride offered by Sherex Chemical Co.
[4]Preservative offered by Glyco, Inc.
[5]Ethylene diamine tetraacetic acid The composition is prepared as follows. The DRO water is first heated to 190° F. The cetyl betaine, Adogen 442-100P, EDTA, monosodium phosphate, and disodium phosphate are added with mixing for about 5 minutes. The silicone gum premix is added with mixing. The Natrosol is added with mixing. The composition is then homogenized with a disperser, e.g., a Gifford-Wood Mill, for about 2 minutes. The composition is then cooled to 150° F. The perfume and Glydant are added with mixing for about 10 minutes. The batch is then cooled to ambient temperature and stored.

EXAMPLE IX

The following is a hair styling rinse composition representative of the present invention.

| Component | Weight % |
| --- | --- |
| Natrosol Plus CS Grade D-67[1] | 1.15 |
| Cetyl Betaine | 0.04 |
| DiTallow DiMethyl Ammonium Chloride (DTDMAC) | 0.75 |
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric The composition is prepared as follows.

The styling polymer premix is prepared by combining the styling polymer, phenyl ethyl pentamethyl disiloxane, and the octamethyl cyclotetrasiloxane.

The silicone gum premix is prepared by combining, in a separate vessel and mixing the silicone gum and the decamethyl cyclopenta siloxane until homogeneous.

About one-half of the DRO water is first heated to about 66° C. The cetyl betaine, citric acid, and sodium citrate are added and mixed until homogeneous. The Natrosol is added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC is added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

EXAMPLE X

The following is a hair styling rinse composition representative of the present invention.

| Component | Weight % |
| --- | --- |
| Natrosol Plus CS Grade D-67[1] | 1.15 |
| Cetyl Betaine | 0.04 |
| DiTallow DiMethyl Ammonium Chloride (DTDMAC) | 0.75 |
| Stearyl Alcohol | 0.2 |
| Cetyl Alcohol | 0.3 |
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| Dextran Purified Crude Grade 2P[4] | 0.75 |
| DRO Water | q.s to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric
[4]Available from D&O Chemicals The composition is prepared as follows.

The styling polymer premix is prepared by combining the styling polymer, phenyl ethyl pentamethyl disiloxane, and the octamethyl cyclotetrasiloxane.

The silicone gum premix is prepared by combining, in a separate vessel and mixing the silicone gum and the decamethyl cyclopenta siloxane until homogeneous.

About one-half of the DRO water is first heated to about 66° C. The cetyl betaine, citric acid, and sodium citrate are added and mixed until homogeneous. The Natrosol and Dextran are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC, stearyl alcohol and cetyl alcohol are added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

EXAMPLE XI

The following is a hair styling rinse composition representative of the present invention.

| Component | Weight % |
| --- | --- |
| Natrosol Plus CS Grade D-67[1] | 1.15 |
| Cetyl Betaine | 0.04 |
| DiTallow DiMethyl Ammonium Chloride (DTDMAC) | 0.75 |

-continued

| Component | Weight % |
|---|---|
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Silicone Gum/Fluid Premix | |
| Polydimethyl Siloxane Gum[3] | 0.30 |
| 350 centistoke Polydimethyl Siloxane Fluid | 0.20 |
| Kathon CG | 0.033 |
| Perfume | 0.2 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric The composition is prepared as follows.

The styling polymer premix is prepared by combining the styling polymer, phenyl ethyl pentamethyl disiloxane, and the octamethyl cyclotetrasiloxane.

The silicone gum/fluid premix is prepared by combining in a separate vessel and mixing the silicone gum and silicone fluid until homogeneous.

About one-half of the DRO water is first heated to about 66° C. The cetyl betaine, citric acid, and sodium citrate are added and mixed until homogeneous. The Natrosol is added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC is added and mixed until homogeneous. The mixture is then cooled to about 43° C. The silicone gum/fluid premix is added and the composition homogenized with a homogenizer (in-line preferred).

The two premixes are then combined and mixed until homogeneous to form the styling rinse composition.

EXAMPLE XXII

The following is a hair styling rinse composition representative of the present invention.

| Component | Weight % |
|---|---|
| Natrosol Plus - Grade 330 | 2.0 |
| Cetyl Betaine | 0.04 |
| DiTallow DiMethyl Ammonium Chloride (DTDMAC) | 0.75 |
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric The composition is prepared as follows.

The styling polymer premix is prepared by combining the styling polymer, phenyl ethyl pentamethyl disiloxane, and the octamethyl cyclotetrasiloxane.

The silicone gum premix is prepared by combining, in a separate vessel and mixing the silicone gum and the decamethyl cyclopenta siloxane until homogeneous.

About one-half of the DRO water is first heated to about 66° C. The cetyl betaine, citric acid, and sodium citrate are added and mixed until homogeneous. The Natrosol is added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC is added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

EXAMPLE XIII

The following is a hair styling rinse composition representative of the present invention.

| Component | Weight % |
|---|---|
| Natrosol Plus CS Grade D-67[1] | 1.15 |
| Cetyl Betaine | 0.04 |
| DiTallow DiMethyl Ammonium Chloride (DTDMAC) | 0.75 |
| Citric Acid | 0.07 |
| Sodium Citrate | 0.17 |
| Styling Polymer Premix - | |
| Styling Polymer[2] | 2.5 |
| Octamethyl Cyclotetrasiloxane | 5.25 |
| Decamethyl Cyclopentasiloxane | 2.25 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric The composition is prepared as follows.

The styling polymer premix is prepared by combining the styling polymer, the octamethyl cyclotetrasiloxane, and the decamethyl cyclopentasiloxane.

The silicone gum premix is prepared by combining, in a separate vessel and mixing the silicone gum and the decamethyl cyclopenta siloxane until homogeneous.

About one-half of the DRO water is first heated to about 66° C. The cetyl betaine, citric acid, and sodium citrate are added and mixed until homogeneous. The Natrosol is added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC is added and mixed until homogeneous. The mixture is then cooled to about 43° C. the silicone gum premix is added and the composition homogenized with a homogenizer (in-line preferred).

The two premixes are then combined and mixed until homogeneous to form the styling rinse composition;

What is claimed is:

1. A cosmetic composition comprising:
   (a) from about 80% to about 100% of a vehicle system which comprises:
      (A) from about 0.1% to about 10.0% by weight of the cosmetic composition of a hydrophobically modified nonionic water-soluble polymer which comprises a water-soluble polymer backbone and hydrophobic groups selected from the group consisting of $C_8$–$C_{22}$ alkyl, aryl alkyl, alkyl aryl groups and mixtures thereof; wherein the ratio of the hydrophilic portion to the hydrophobic portion of the polymer is from about 10:1 to about 1000:1; and
      (B) from about 0.02% to about 0.3% by weight of the cosmetic composition of a water-soluble surfactant having a molecular weight less than about 20,000; and
      (C) from about 65% to about 99% by weight of the cosmetic composition of a compatible solvent; and
   (b) from 0% to about 20%, by weight, of an active cosmetic component; wherein said cosmetic compositions comprise no more than about 1.0% total of water-soluble surfactant materials.

2. The composition of claim 1 wherein said hydrophobically modified nonionic water-soluble polymer comprises a nonionic cellulose ether having a sufficient degree of nonionic substitution, selected from the group consisting of methyl, hydroxyethyl, and hydroxypropyl, to cause it to be water-soluble and being further substituted with a long chain alkyl radical having 10 to 22 carbon atoms in an amount between about 0.2 weight percent and the amount which renders said cellulose ether less than 1% by weight soluble in water.

3. The composition of claim 2 wherein the vehicle system provides a rheology to the cosmetic composition that is characterized by a shear stress of from 0 to about 50 pascal over a shear rate range of from about 0.04 sec$^{-1}$ to about 25 sec$^{-1}$.

4. The composition of claim 3 wherein the nonionic cellulose ether comprises from about 0.2% to about b 5.0% of the cosmetic composition.

5. The composition of claim 4 wherein the nonionic cellulose ether comprises the long-chain alkyl radical attached via an ether linkage.

6. The composition of claim 5 wherein the cellulose ether comprises a water-soluble hydroxypropyl cellulose substituted with a long-chain alkyl radical having 10 to 22 carbon atoms in an amount between about 0.2 weight percent and the amount which renders the hydroxypropyl cellulose less than 1% by weight soluble in water.

7. The composition of claim 6 wherein the nonionic cellulose ether comprises a water-soluble hydroxyethyl cellulose substituted with a long-chain alkyl radical having 10 to 22 carbon atoms in an amount between about 0.2 weight percent and the amount which renders the hydroxyethyl cellulose less than 1% by weight soluble in water.

8. The composition of claim 7 wherein the hydroxyethyl cellulose prior to substitution with the long chain alkyl group has a molecular weight of about 50,000 to 700,000.

9. The composition of claim 8 wherein the water-soluble hydroxyethyl cellulose is substituted with a long chain alkyl radical having about 16 carbon atoms in a n amount between about 0.40% to about 0.95%, by weight; the hydroxyethyl molar substitution is from about 2.3 to about 3.7; and the average molecular weight of the unsubstituted cellulose is from about 300,000 to about 700,000.

10. The composition of claim 3 which comprises from about 0.05% to about 0.3% of the water-soluble surfactant.

11. The composition of claim 10 wherein the water-soluble surfactant is selected from the group consisting of cetyl betaine, ammonium lauryl sulfate, ammonium laureth sulfate, cetyl trimethyl ammonium chloride, and mixtures thereof.

12. The composition of claim 3 which additionally comprises from about 0.3% to about 5.0% of a water-soluble polymeric material having a molecular weight greater than about 20,000.

13. The composition of claim 12 wherein the water-soluble polymeric material is selected from the group consisting of hydroxyethyl cellulose, hydroxypropyl cellulose, hydroxypropyl methyl cellulose, polyethylene glycol, polyacrylamide, polyacrylic acid, polyvinyl alcohol, polyvinyl pyrrolidone, dextran, carboxymethyl cellulose, acacia plant exudate, ghatti plant exudate, tragacanth plant exudate, sodium alginate, propylene glycol alginate, sodium carrageenan, natural polysaccharides, and mixtures thereof.

14. The composition of claim 13 wherein the water-soluble polymeric material comprises a natural polysaccharide.

15. The composition of claim 14 wherein the natural polysaccharide is selected from the group consisting of guar gum, locust bean gum, xanthan gum, and mixtures thereof.

16. The composition of claim 3 which additionally comprises from about 0.05% to about 1.0% by weight of the composition of a chelating agent.

17. The composition of claim 16 wherein the chelating agent is selected from the group consisting of ethylene diaminetetracetic acid and salts thereof, nitriloacetic acid and salts thereof, hydroxyethylene diamine triacetic acid and salts thereof, diethylene triaminepenta-acetic acid and salts thereof, diethanolglycine and salts thereof, ethanol diglycine and salts thereof, citric acid and salts thereof, and phosphoric acid and salts thereof.

18. The composition of claim 12 which additionally comprises from about 0.05% to about 3% by weight of the composition of a chelating agent.

19. The composition of claim 18 wherein the chelating agent is selected from the group consisting of ethylene diaminetetracetic acid and salts thereof, nitriloacetic acid and salts thereof, hydroxyethylene diamine triacetic acid and salts thereof, diethylene triaminepenta-acetic acid and salts thereof, diethanolglycine and salts thereof, ethanol diglycine and salts thereof, citric acid and salts thereof, and phosphoric acid and salts thereof.

20. The composition of claim 12 wherein from bout 0.02% to about 2.5% of the water-soluble polymer is selected from the group consisting of water-soluble polymeric materials having a molecular weight greater than about 1,000,000, and water-soluble polymeric materials having strong ionic character.

21. The composition of claim 16 wherein from about 0.02% to about 2.5% of the water-soluble polymer is selected from the group consisting of water-soluble polymeric materials having a molecular weight greater than about 1,000,000, and water-soluble polymeric materials having strong ionic character.

22. The composition of claim 18 wherein from about 0.02% to about 2.5% of the water-soluble polymer is selected from the group consisting of water-soluble polymeric materials having a molecular weight greater than 1,000,000, and water-soluble polymeric materials having strong ionic character.

23. The cosmetic composition of claim 3 which is a hair care composition wherein said active component comprises an active hair care component.

24. The composition of claim 23 wherein the composition comprises no more than bout 1% of fatty alcohol materials.

25. The composition of claim 24 wherein the active hair care component is selected from the group consisting of conditioning agents, antidandruff aids, hair growth promoters, perfumes, dyes, pigments, hair holding polymers, and mixtures thereof.

26. The composition of claim 25 wherein the active hair care component is selected from the group consisting of a volatile silicone fluid having a viscosity at 25° C. of less than about 10 centipoise, a non-volatile silicone fluid having a viscosity at 25° C. of less than about 100,000 cP; a silicone gum having a viscosity at 25° C. greater than about 1,000,000 cP, and mixtures thereof.

27. The composition of claim 26 wherein the silicone gum is selected from the group consisting of polydimethylsiloxane gums and polyphenyl methyl siloxane gums.

28. The composition of claim 25 wherein the active hair care component comprises from about 0.01% to bout 10% of a rigid silicone polymer having a complex viscosity at 25° C. of at least $2 \times 10^5$ poise.

29. The composition of claim 28 which additionally comprises a volatile carrier for the rigid silicone polymer.

30. A hair care composition according to claim 29 wherein the rigid silicone polymer is selected from the group consisting of organic substituted siloxane gums, silicone elastomers, filler reinforced polydimethyl siloxane gums, resin reinforced siloxanes and crosslinked siloxane polymers.

31. A hair care composition according to claim 30 wherein the volatile carrier is a cyclic silicone containing from about 3 to about 7 silicon atoms.

32. A hair care composition according to claim 31 wherein the rigid silicone polymer is a silicone elastomer and the sole volatile carrier is water.

33. A hair care composition according to claim 31 wherein the rigid silicone polymer is a filler reinforced polydimethyl siloxane gum.

34. A hair care composition according to claim 31 wherein the rigid silicone polymer is an organic substituted siloxane gum.

35. A hair care composition according to claim 31 wherein the rigid silicone polymer is a resin reinforced siloxane.

36. The composition of claim 25 wherein the active hair care component comprises from about 0.1% to bout 10.0% of a copolymer which has a vinyl polymeric backbone having grafted to it monovalent siloxane polymeric moieties, said copolymer comprising C monomers and components selected from the group consisting of A monomers, B monomers, and mixtures thereof, wherein:

A is at least one free radically polymerizable vinyl monomer, the amount by weight of A monomer, when used, being up to about 98% by weight of the total weight of all monomers in said copolymer;

B is at least one reinforcing monomer copolymerizable with Z, the amount by weight of B monomer, when used, being up to about 98% of the total weight of all monomers in said copolymer, said B monomer being selected from the group consisting of polar monomers and macromers; and C is a polymeric monomer having a molecular weight of from about 1,000 to about 50,000 and the general formula

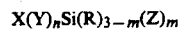

wherein
X is a vinyl group copolymerizable with the A and B monomers
Y is a divalent linking group
R is a hydrogen, lower alkyl, aryl or alkoxy
Z is a monovalent siloxane polymeric moiety having a number average molecular weight of at least about 500, is essentially unreactive under copolymerization conditions, and is pendant from said vinyl polymeric backbone after polymerization
n is 0 or 1
m is an integer from 1 to 3
wherein C comprises from bout 0.01% to bout 50% of the copolymer.

37. The composition of claim 36 wherein the copolymer comprises from about 5% to about 98% A monomer, from about 0.1% to about 50% monomer, and from 0% to about 98% B monomer.

38. The composition of claim 25 wherein the active hair care component comprises a lipophilic free radically polymerizable vinyl monomer or a hydrophilic monomer which is copolymerizable with A, or a mixture thereof, and a silicone-containing macromer having a weight average molecular weight of from bout 1,000 to bout 50,000 based on polydimethylsiloxane selected from the group consisting of

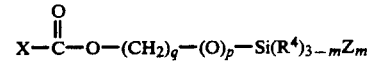

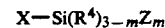

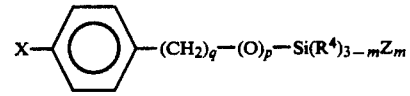

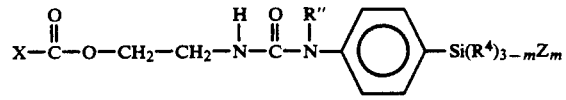

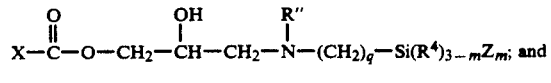

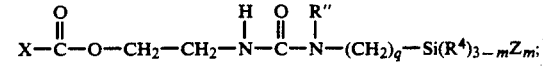

wherein m is 1, 2 or 3; p is 0 or 1; R" is alkyl or hydrogen; q is an integer from 2 to 6; s is an integer from 0 to 2; X is

R$^1$ is hydrogen or —COO; R$^2$ is hydrogen, methyl or —C$_2$COO; Z is

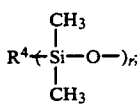

R$^4$ is alkyl, alkoxy, alkylamino, aryl, or hydroxyl; and r is an integer from 5 to bout 700.

39. A hair care composition according to claim 38 wherein monomer A is selected from the group consisting of acrylic acid esters of C$_1$-C$_{18}$ alcohols, methacrylic acid esters of C$_1$-C$_{18}$ alcohols, styrene, vinyl acetate, vinyl chloride, vinylidene chloride, acrylonitrile, alpha-methylstyrene, t-butylstyrene, butadiene, cyclohexadiene, ethylene, propylene, vinyl toluene, polystyrene macromer, and mixtures thereof.

40. A hair care composition according to claim 39 wherein monomer B is selected from the group consisting of acrylic acid, methacrylic acid, N,N-dimethylacrylamide, dimethylaminoethyl methacrylate, quaternized dimethylaminoethyl methacrylate, methacrylonitrile, methacryloamide, maleic anhydride, half esters of maleic anhydride, itaconic acid, acrylamide, acrylate alcohols, hydroxyethyl methacrylate, diallyldimethyl ammonium chloride, vinyl pyrrolidone, vinyl ethers maleimides, acylactones, 2-ethyl-2-oxazoline, vinyl pyridine, vinyl imidazole, styrene sulfonate, and mixtures thereof.

41. A hair care composition according of claim 37 wherein monomer A is selected from the group consisting of N-butylmethacrylate, isobutylmethacrylate, 2-ethylhexyl methacrylate, t-butylacrylate, t-butylmethacrylate, methylmethacrylate, and mixtures thereof.

42. A hair care composition according to claim 41 wherein monomer B is selected from the group consisting of acrylic acid, N,N-dimethylacrylamide, dimethylaminoethyl methacrylate, quaternized dimethylaminoethyl methacrylate, vinyl pyrrolidone, and mixtures thereof.

43. A hair care composition according to claim 42 wherein monomer C has the formula

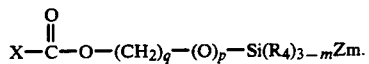

44. A hair care composition according to claim 43 wherein p = 0 and q = 3.

45. A hair care composition according to claim 44 wherein m is 1, r is about 250, R$^4$ is alkyl, R$_1$ is hydrogen and R$^2$ is methyl.

46. A hair care composition according to claim 40 wherein the silicone-containing copolymer is selected from the group consisting of
acrylic acid/n-butylmethacrylate/polydimethylsiloxane macromer-20,000 mw (10/70/20);
N,N-dimethylacrylamide/isobutyl methacrylate/PDMS macromer-20,000 ms (20/60/20);
dimethylaminoethyl methacrylate/isobutyl methacrylate/2-ethylhexyl methacrylate/PDMS-20,000 mw (25/40/15/20);
dimethylaminoethyl methacrylate/isobutyl methacrylate/PDMS-20,000 mw (10/70/20);
quaternized dimethylaminoethyl methacrylate/isobutyl methacrylate/PDMS-20,000 mw (40/40/20);
acrylic acid/methyl methacrylate/PDMA-20,000 mw (40/40/20);
acrylic acid/isopropyl methacrylate/PDMS-20,000 mw (25/65/10);
N,N-dimethylacrylamide/methoxyethyl methacrylate/PDMS-20,000 mw (60/2515);
dimethylacrylamide/PDMS macromer-20,000 mw (80/20);
t-butylacrylate/t-butylmethacrylate/PDMS macromer-10,000 mw (56/24/20);
t-butylacrylate/PDMS macromer-10,000 mw (80/20);
t-butylacrylate/N,N-dimethylacrylamide/PDMS macromer-10,000 mw (70/10/20);
t-butylacrylate/acrylic acid/PDMS macromer-10,000 mw (75/5/20); and mixtures thereof.

47. A hair care composition comprising:
(a) from about 80% to about 99.9%, by weight of the hair care composition, of a vehicle system which comprises:
  (A) from about 0.2% to bout 5.0%, by weight of the hair care composition, of a nonionic cellulose ether having a hydroxyethyl molar substitution of from about 2.3% to about 3.7%, and being further substituted with a C$_{16}$ alkyl group at from about 0.40% is about 0.95%, by weight, wherein the unsubstituted hydroxyethyl cellulose has an average molecular weight of from about 300,000 to bout 700,000;
  (B) from about 0.05% to about 0.3%, by weight of the hair care composition, of a water-soluble surfactant, having a molecular weight less than about 20,000, which is selected from the group consisting of cetyl betaine, ammonium lauryl sulfate, ammonium laureth sulfate, cetyl trimethyl ammonium chloride, and mixtures thereof;
  (C) from about 0.05% to about 0.3%, of a chelating agent which is selected from the group consisting of ethylene diamine tetra acetic acid and salts thereof, citric acid and salts thereof, and phosphoric acid and salts thereof;
  (D) from about 0.05% to about 1.0% of a distributing aid which is selected from the group consisting of xanthan gum and dextran having a molecular weight greater than about 1,000,000; and
  (E) from about 65% to about 99% by weight of the hair care composition of a compatible solvent; and
(b) from about 0.1% to about 20%, by weight of the hair care composition, of an active hair care component; wherein said hair care composition comprises no more than about 0.5% total of water-soluble surfactants; no more than about 1% of fatty alcohol materials; and wherein said hair care composition has a rheology that is characterized by a shear stress of from 0 to about 50 pascal over a shear rate range of from about 0.04 sec$^{-1}$ to about 25 sec$^{-1}$.

48. The composition of claim 47 wherein the active hair care component comprises a silicone-containing copolymer selected from the group consisting of acrylic acid/n-butylmethacrylate/polydimethylsiloxane macromer-20,000 mw (10/70/20);
N,N-dimethylacrylamide/isobutyl methacrylate/PDMS macromer-20,000 mw (20/60/20));
dimethylaminoethyl methacrylate/isobutyl methacrylate/2l-ethylhexyl methacrylate/PDMS-20,000 mw (25/40/15/20);
dimethylaminoethyl methacrylate/isobutyl methacrylate/PDMS-20,000 mw (10/70/20);
quaternized dimethylaminoethyl methacrylate/isobutyl methacrylate/PDMS-20,000 mw (40/40/20);
acrylic acid/methyl methacrylate/PDMS-20,000 mw (40/40/20);
acrylic acid/isopropyl methacrylate/PDMS-20,000 mw (25/65/10);
N,N-dimethylacrylamide/methoxyethyl methacrylate/PDMS-20,000 mw (60/25/15);
dimethylacrylamide/PDMS macromer-20,000 mw (80/20);
t-butylacrylate/t-butylmethacrylate/PDMS macromer-10,000 mw (56/24/20);
t-butylacrylate/PDMS macromer-10,000 mw (80/20);
t-butylacrylate/N,N-dimethylacrylamide/PDMS macromer-10,000 mw (70/10/20);
t-butylacrylate/acrylic acid/PDMS macromer-10,000 mw (75/5/20); and mixtures thereof.

49. The composition of claim 47 wherein the active hair care component comprises a silicone conditioning agent which is selected from the group consisting of a conditioning agent comprising, by weight of the hair care composition:
(a) from about 0.1% to about 2.5% of a polydimethylsiloxane gum;
(b) from about 0.02% to about 0.7% of fumed silica; and
(c) from about 0.4% to about 18% of a volatile carrier; a conditioning agent comprising:
(a) a volatile silicone fluid having a viscosity at 25° C. of less than about 10 centipoise;
(b) from about 0.5% to bout 2.0% of a silicone gum having a viscosity at 25° C. of greater than about 1,000,000 centipoise;
at ratios of volatile fluid to gum of from bout 85:15 to about 50:50; and
conditioning agent comprising:
(a) a non-volatile silicone fluid having a viscosity at 25° C. of less than about 100,000 centipoise;
(b) from about 0.5% to about 2.0% of a silicone gum having a viscosity at 25° C. of greater than 1,000,000 centipoise;
at ratios of non-volatile fluid to gum of from about 60:40 to about 40:60.

* * * * *